United States Patent
Menard et al.

(10) Patent No.: US 7,208,522 B1
(45) Date of Patent: *Apr. 24, 2007

(54) METHODS AND COMPOSITIONS FOR THE PREVENTION AND TREATMENT OF SYNDROME X

(75) Inventors: Michael Menard, Gurnee, IL (US); Susie Rockway, Grayslake, IL (US)

(73) Assignee: Pharmanutrients, Lake Bluff, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/333,297

(22) PCT Filed: Aug. 2, 2000

(86) PCT No.: PCT/US00/21044

§ 371 (c)(1),
(2), (4) Date: Jul. 3, 2003

(87) PCT Pub. No.: WO02/09691

PCT Pub. Date: Feb. 7, 2002

(51) Int. Cl.
*A61K 31/20* (2006.01)

(52) U.S. Cl. .................................... 514/560
(58) Field of Classification Search ................ 514/560
See application file for complete search history.

(56) References Cited

U.S. PATENT DOCUMENTS

| 4,981,844 | A | 1/1991 | Alexander et al. |
| 5,603,959 | A | 2/1997 | Horrobin et al. |
| 5,886,037 | A | 3/1999 | Klor et al. |
| 6,060,514 | A | 5/2000 | Jerome et al. |
| 6,214,820 | B1 * | 4/2001 | Jeppesen et al. ......... 514/211.11 |
| 6,417,212 | B1 * | 7/2002 | Brooks et al. ............. 514/374 |
| 6,509,374 | B2 * | 1/2003 | Sauerberg et al. ......... 514/533 |

FOREIGN PATENT DOCUMENTS

WO     WO 99/29317     6/1999

OTHER PUBLICATIONS

Houseknecht et al., "Dietary Conjugated Linoleic Acid Normalizes Impaired Glucose Tolerance in the Zucker Diabetic Fatty fa/fa Rat", Biochemical and Biophysical Research Communications 244, 678-682 (1998), Article No. RC988303.*
Medline Abstract No. 93164679, Hjermann, Journal of Cardiovascular Pharmacology, (1992), 20 Suppl. 8, S5-10.*
Stedman's Medical Dictionary, 25th Edition, published 1990 by Williams & Wilkins, (MD), p. 1487, "Stress".*
U.S. Appl. No. 10/333,299, filed Jan. 17, 2003, Menard et al.
U.S. Appl. No. 10/333,297, filed Jan. 17, 2003, Menard et al.
U.S. Appl. No. 10/333,298, filed Jan. 17, 2003, Menard et al.
U.S. Appl. No. 10/333,295, filed Jan. 17, 2003, Menard et al.

* cited by examiner

*Primary Examiner*—Raymond J. Henley, III
(74) *Attorney, Agent, or Firm*—Bell, Boyd & Lloyd LLP

(57) ABSTRACT

Methods and compositions for preventing or treating Syndrome X are provided. The method includes administering a therapeutically effective amount of conjugated linoleic acid.

9 Claims, No Drawings

METHODS AND COMPOSITIONS FOR THE PREVENTION AND TREATMENT OF SYNDROME X

BACKGROUND OF THE INVENTION

The present invention relates generally to compositions and methods for the treatment of disease states. More specifically, the present invention relates to compositions and methods for treating or preventing insulin-resistance syndrome (Syndrome X).

Syndrome X is a term that has been given to a group of metabolic abnormalities consisting of multiple metabolic aberrations. These metabolic abnormalities have also been referred to as insulin-resistance syndrome and metabolic syndrome. The metabolic aberrations that fall under the designation Syndrome X include insulin-resistance (impaired glucose tolerance) and hyperinsulinemia. Other concomitant aberrations occurring in Syndrome X may include, but are not limited to, high plasma triglyceride levels, a low high density lipoprotein profile, microvascular angina, hypertension and obesity.

During the past two decades, low-fat high-carbohydrate diets have been advocated by health care professionals. Despite the focus on improved nutrition during this period, society has experienced an increase in the number of individuals becoming obese. One possible explanation for this phenomena may relate to the impaired ability of individuals with the propensity towards Syndrome X to process elevated carbohydrate intake associated with these diets. Thus, these "healthy diets" may actually cause individuals with this syndrome to gain weight. This may be due in part to the insulin resistance associated with Syndrome X.

It has been proposed that one of the underlying factors of Syndrome X includes an inability of the enzyme lipoprotein lipase to effectively clear chylomicrons from the plasma after digestion of dietary fat. It is interesting to note that there is a genetic disorder known as Familial Lipoprotein Lipase Deficiency, which is an autosomal recessive disorder. While homozygous expression of this disorder is uncommon with an occurrence of 1 in a million, the occurrence of the heterozygous form of this disorder is approximately 1 in 500.

Further, heterozygote first-degree relatives of patients with LPL deficiency exhibit a 50% decrease of LPL activity in plasma compared to controls under test conditions, while only exhibiting mild plasma lipid elevations. Additionally, several studies have suggested that association of this disorder or a predilection thereto may be involved in a much wider incidence of associated metabolic disturbances. There may actually be a substantial range of genetically-based lipoprotein lipase response, which may relate to a spectrum of response in individuals susceptible to Syndrome X. Additionally, the interaction of other lifestyle circumstances and metabolic conditions may accentuate this susceptibility.

In patients with Syndrome X, as well as in many patients diagnosed with hypertension, obesity, and type II diabetes, elevated levels of IL-1, IL-6, and TNF-alpha have been reported. IL-6 has been demonstrated to be the main cytokine mediator of the acute-phase response. This action of IL-6 as a prime inducer of acute-phase response, resulting in the action of cytokines on many tissues, may be a major contributor to physiological and clinical features of Syndrome X.

Along with the elevation of these cytokines, patients with Syndrome X may also exhibit elevated glucagon and cortisol concentrations. In patients diagnosed with Syndrome X, there are accompanying metabolic abnormalities, which likely accentuate the expression of Syndrome X by further inhibiting the ability of the body to process glucose optimally. There is evidence of significant variation of tissue sensitivity and response to cortisol in patients with Syndrome X, suggesting that even minimally elevated cortisol levels may be related to hypertension, insulin resistance, glucose intolerance, and hypertriglyceridemia.

The inventors do not believe that there is an effective treatment for patients suffering from Syndrome X.

Accordingly, there is a need for improved methods of treatment and compositions for treating Syndrome X.

SUMMARY OF THE INVENTION

The present invention relates to methods and compositions for the attenuation and prevention of Syndrome X. In this regard, the present invention can be used to deal with many of the underlying physiological abnormalities associated with Syndrome X, and to provide a physiologically based means to aid in attenuating the insulin resistance and hyperinsulinemia associated with this disorder.

To this end, in an embodiment the present invention provides a method for treating Syndrome X in an individual suffering from same. The method comprises the step of administering a therapeutically effective amount of a composition including conjugated linoleic acid.

In an embodiment, approximately 0.5 to about 10 grams per day of conjugated linoleic acid are administered.

In an embodiment, the conjugated linoleic acid is either a pure isomer of octadecadienoic acid, or a mixture of octadecadienoic acid isomers selected from the group consisting of: cis-8, cis-10; cis-8, trans-10; trans-8, cis-10; trans-8, trans-10; cis-9, cis-11; cis-9, trans-11; trans-9, cis-11; trans-9, trans-11; cis-10, cis-12; cis-10, trans-12; trans-10, cis-12; trans-10, trans-12; cis-11, cis-13; cis-11, trans-13; trans-11, cis-13; trans-11, trans-13 octadecadienoic acid; metabolites thereof, including but not limited to 18:3 cis-6, cis-9, trans-11; 18:3 cis-6, trans-10, cis-12; 18:3 cis-8, trans-12, cis-14; 20:3 cis-8, cis-11, trans-13; 20:4 cis-5, cis-8, cis-11, trans-13; 20:4 cis-5, cis-8, trans-12, cis-14; as well as precursors or derivatives thereof.

In an embodiment, the composition includes a flavor.

In an embodiment, the composition includes an artificial sweetener.

In another embodiment of the present invention, a method of reducing the symptoms associated with Syndrome X in an individual having same is provided comprising the step of administering a therapeutically effective amount of a composition including conjugated linoleic acid.

In an embodiment, approximately 0.5 to about 10 grams per day of conjugated linoleic acid are administered.

In an embodiment, the conjugated linoleic acid is either a pure isomer of octadecadienoic acid, or a mixture of octadecadienoic acid isomers selected from the group consisting of: cis-8, cis-10; cis-8, trans-10; trans-8, cis-10; trans-8, trans-10; cis-9, cis-11; cis-9, trans-11; trans-9, cis-11; trans-9, trans-11; cis-10, cis-12; cis-10, trans-12; trans-10, cis-12; trans-10, trans-12; cis-11, cis-13; cis-11, trans-13; trans-11, cis-13; trans-11, trans-13 octadecadienoic acid; metabolites thereof, including but not limited to 18:3 cis-6, cis-9, trans-11; 18:3 cis-6, trans-10, cis-12; 18:3 cis-8, trans-12, cis-14; 20:3 cis-8, cis-11, trans-13; 20:4 cis-5, cis-8, cis-11, trans-13; 20:4 cis-5, cis-8, trans-12, cis-14; as well as precursors or derivatives thereof.

In an embodiment, the composition includes a flavor.

In an embodiment, the composition includes an artificial sweetener.

In yet another embodiment of the present invention, a method of treating hyperinsulinemia is provided comprising the step of administering a therapeutically effective amount of a composition including conjugated linoleic acid.

In an embodiment, approximately 0.5 to about 10 grams per day of conjugated linoleic acid are administered.

In an embodiment, the conjugated linoleic acid is either a pure isomer of octadecadienoic acid, or a mixture of octadecadienoic acid isomers selected from the group consisting of: cis-8, cis-10; cis-8, trans-10; trans-8, cis-10; trans-8, trans-10; cis-9, cis-11; cis-9, trans-11; trans-9, cis-11; trans-9, trans-11; cis-10, cis-12; cis-10, trans-12; trans-10, cis-12; trans-10, trans-12; cis-11, cis-13; cis-11, trans-13; trans-11, cis-13; trans-11, trans-13 octadecadienoic acid; metabolites thereof, including but not limited to 18:3 cis-6, cis-9, trans-11; 18:3 cis-6, trans-10, cis-12; 18:3 cis-8, trans-12, cis-14; 20:3 cis-8, cis-11, trans-13; 20:4 cis-5, cis-8, cis-11, trans-13; 20:4 cis-5, cis-8, trans-12, cis-14; as well as precursors or derivatives thereof.

In a still further embodiment of the present invention, a method of preventing Syndrome X is provided comprising the step of administering a therapeutically effective amount of a composition including conjugated linoleic acid to an individual at risk for Syndrome X.

An advantage of the present invention is that it provides a method and composition for the attenuation of Syndrome X.

A further advantage of the present invention is that it provides a method for attempting to prevent Syndrome X.

An additional advantage of the present invention is that it provides a method and composition for treating hyperinsulinemia.

Another advantage of the present invention is that it provides a method and composition for treating insulin-resistance.

Furthermore, an advantage of the present invention is that it provides a method for preventing or treating chronic obesity.

Moreover, an advantage of the present invention is that it provides a method for attenuating metabolic abnormalities.

These and other advantages and features present invention will be described in and apparent from the detailed description of the presently preferred embodiments.

DETAILED DESCRIPTION OF PRESENTLY PREFERRED EMBODIMENTS

The present invention provides methods and compositions for the attenuation and prevention of Syndrome X. As noted above, Syndrome X is a group of metabolic abnormalities that includes insulin resistance. Pursuant to the present invention, a therapeutically effective amount of conjugated linoleic acid is administered to an individual suffering from or at risk of Syndrome X.

Conjugated linoleic acid as used in this invention is intended to influence those physiological processes associated with induction and maintenance of Syndrome X. Conjugated linoleic acid is believed to be effective, through its modulating effect on specific cytokines and pro-inflammatory prostaglandins. Conjugated linoleic acid minimizes the expression of IL-1, IL-6, TNFα, and $PGE_2$. Additionally, conjugated linoleic acid has an effect on PPAR-α to modulate glucose levels. While these compounds are associated with inflammatory responses, their influence on the effect of these compounds on increases in cortisol, catecholamines, glucagon, and other insulin-resistance associated compounds is less well understood. In its intended application, conjugated linoleic acid, a specific isomer or ratio of isomers, or a metabolite thereof would be administered over a period of time as a means to diminish the symptoms of Syndrome X.

Conjugated linoleic acid refers to a group of dienoic derivatives of linoleic acid that occur naturally in milk and the meat of ruminant animals. It can be synthesized in the laboratory and is available commercially as a dietary supplement and has been shown to be nontoxic.

Conjugated linoleic acid acts on body composition, resulting in an increased lean body mass and decrease in adipose tissue, by enhancing uptake and utilization of lipids. Mechanisms for these effects appear to be related to conjugated linoleic acid activating hormone sensitive lipase within adipose tissue and inhibiting the effect of lipoprotein lipase located on the endothelial wall of the capillaries surrounding the adipose tissue. Within Syndrome X, the effect of conjugated linoleic acid to enhance hormone sensitive lipase activity enhances the release and utilization of elevated lipids for energy, and may decrease the extent of hyperlipidemia in susceptible populations.

Additionally, conjugated linoleic acid is believed to normalize impaired glucose tolerance and improve hyperinsulinemia. Conjugated linoleic acid favorably influences the physiological response to stress, particularly inflammatory eicosanoids and catabolic cytokines. Conjugated linoleic acid appears to modulate the immune system under conditions where COX-2 enzyme is induced by suppressing PGE-2 production. The mechanism for the observed anti-inflammatory effects of conjugated linoleic acid in various animal models has been associated with reduced arachidonic acid, a precursor for PGE-2 accumulation in cell membranes. Any effect conjugated Linoleic acid has on the synthesis of eicosanoids should correlate with uptake into neutral phospholipids by cells. Conjugated linoleic acid can be readily incorporated in a dose-dependent manner into the tissues of animals consuming diets containing conjugated linoleic acid, with a concomitant reduction of arachidonic acid. Conjugated linoleic acid may have an additional role in addressing Syndrome X symptoms by reducing serum triglycerides and cholesterol as well as decreasing plaque formation in hamsters and rabbits.

As noted above, the present invention provides method and composition for patients suffering from Syndrome X. Conjugated linoleic acid is intended to influence those physiological processes associated with the induction and maintenance of Syndrome X. It is intended that the conjugated linoleic acid will be administered over a period of time as a means to diminish the insulin resistance associated with chronic obesity and specifically Syndrome X. The ingredients that are used in the compositions of present invention are preferably all naturally occurring substances or derivatives thereof; the active ingredients are all naturally occurring substances or derivatives thereof. The composition can be a pharmaceutical product, a nutritional supplement, or an over the counter product.

Pursuant to the present invention, the method and composition comprises administering conjugated linoleic acid. If desired, the composition can include non-active ingredients and/or agents such as flavors, artificial sweeteners, excipients, etc. This product is intended to provide a physiologically based means to aid in maintaining normal plasma glucose levels and normal insulin respons Conjugated linoleic acid is believed to be absorbed efficiently into the body in a manner similar to that of other fatty acids, e.g., linoleic acid. The safety of conjugated linoleic acid has been demonstrated in detailed toxicological assessments. It is believed that conjugated linoleic acid is safe for human consumption.

There are a variety of mixtures of conjugated linoleic acid that can be used as well as methods for making same. By way of example, U.S. Pat. No. 5,986,116, the disclosure of which is incorporated herein by reference, discloses a preferred method for producing conjugated linoleic acid.

By way of example and not limitation, an example of the product is as follows: as a tablet, the product would include 0.5 to 1 g conjugated linoleic acid and the following flavors and excipients: magnesium stearate, silicone dioxide, croscarmelose sodium, stearic acid, microcrystalline cellulose, calcium phosphate, silicon dioxide, dextran, aqueous base film coat.

In a preferred embodiment of the method of the present invention, a sufficient amount of product is provided so that an individual receives approximately:

0.5 to 10 grams of conjugated linoleic acid per day.

In a most preferred embodiment, sufficient product is administered so the patient receives 3 to 6 grams of conjugated linoleic acid per day. It is believed that at this level the symptoms associated with Syndrome X will be at least reduced if not eliminated.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

We claim:

1. A method of reducing inflammation associated with stress response of Syndrome X in an individual having same comprising the step of administering a therapeutically effective amount of a composition including conjugated linoleic acid.

2. The method of claim 1 wherein approximately 0.5 to about 10 grams per day of conjugated linoleic acid are administered.

3. The method of claim 1 wherein the conjugated linoleic acid is selected from the group consisting of: pure isomer of octadecadienoic acid; mixtures of octadecadienoic acid isomers cis-8, cis-10; cis-8, trans-10; trans-8, cis 10; trans-8, trans-10; cis-9, cis-11; cis-9, trans-11; trans-9, cis-11; trans-9, trans-11; cis-10, cis-12; cis-10, trans-12; trans-10, cis-12; trans-10-trans-12; cis-11, cis-13; cis-11, trans-13; trans-11, cis-13; trans-11, trans-13 octadecadienoic acid; 18:3 cis-6, cis-9, trans 11; 18:3 cis-6, trans-10, cis-12; 18:3 cis-8, trans-12, cis-14; 20:3 cis-8, cis-11, trans-13; 20:4 cis-5, cis-8, cis-11, trans-13; 20:4 cis-5, cis-8, trans-12, cis-14; metabolites thereof; and precursors and derivatives thereof.

4. The method of claim 1 wherein the composition includes a flavor.

5. The method of claim 1 wherein the composition includes an artificial sweetener.

6. A method of reducing inflammation associated with stress response in an individual having same comprising the step of administering a therapeutically effective amount of a composition including conjugated linoleic acid.

7. The method of claim 6 wherein approximately 0.5 to about 10 grams per day of conjugated linoleic acid are administered.

8. The method of claim 6 wherein the conjugated linoleic acid is selected from the group consisting of: pure isomer of octadecadienoic acid; mixtures of octadecadienoic acid isomers cis-8, cis-10; cis-8, trans-10; trans-8, cis-10; trans-8, trans-10; cis-9, cis-11; cis-9, trans-11; trans-9, cis-11; trans-9, trans-11; cis-10, cis-12; cis-10, trans-12; trans-10, cis-12; trans-10-trans-12; cis-11, cis-13; cis-11, trans-13; trans-11, cis-13; trans-11, trans-13 octadecadienoic acid; 18:3 cis-6, cis-9, trans 11; 18:3 cis-6, trans-10, cis-12; 18:3 cis-8, trans-12, cis-14; 20:3 cis-8, cis-11, trans-13; 20:4 cis-5, cis-8, cis-11, trans-13; 20:4 cis-5, cis-8, trans-12, cis-14; metabolites thereof; and precursors and derivatives thereof.

9. The method of claim 6 wherein the stress response is associated with Syndrome X.

* * * * *